United States Patent
Yoshino

(10) Patent No.: US 7,931,587 B2
(45) Date of Patent: Apr. 26, 2011

(54) ENDOSCOPE WITH DECREASED STRAY LIGHT EFFECT THAT INCLUDES A LIGHT SHIELDING MEMBER THAT DOES NOT PASS ANY LIGHT RAYS EMITTED FROM AN ILLUMINATOR

(75) Inventor: Koichiro Yoshino, Fuchu (JP)

(73) Assignee: Olympus Medical Systems Corp., Tokyo (JP)

( * ) Notice: Subject to any disclaimer, the term of this patent is extended or adjusted under 35 U.S.C. 154(b) by 1152 days.

(21) Appl. No.: 11/474,937

(22) Filed: Jun. 27, 2006

(65) Prior Publication Data
US 2007/0004966 A1    Jan. 4, 2007

(30) Foreign Application Priority Data

Jun. 29, 2005   (JP) .................................. 2005-189346

(51) Int. Cl.
*A61B 1/00* (2006.01)
(52) U.S. Cl. ........ 600/129; 600/109; 600/160; 600/176; 600/177
(58) Field of Classification Search .................. 600/152, 600/177–179, 176, 129–130, 160, 164, 476, 600/181
See application file for complete search history.

(56) References Cited

U.S. PATENT DOCUMENTS

| | | | |
|---|---|---|---|
| 6,240,312 B1 * | 5/2001 | Alfano et al. ................. | 600/476 |
| 6,836,377 B1 * | 12/2004 | Kislev et al. ................. | 359/708 |
| 2002/0109774 A1 * | 8/2002 | Meron et al. .................... | 348/74 |
| 2003/0028078 A1 * | 2/2003 | Glukhovsky .................. | 600/109 |
| 2003/0130562 A1 * | 7/2003 | Barbato et al. ............... | 600/109 |
| 2003/0171652 A1 * | 9/2003 | Yokoi et al. ................... | 600/160 |
| 2004/0225190 A1 * | 11/2004 | Kimoto et al. ................ | 600/177 |
| 2005/0043586 A1 * | 2/2005 | Suzushima ................... | 600/160 |
| 2006/0030752 A1 | 2/2006 | Orihara | |

FOREIGN PATENT DOCUMENTS

JP      2001-91860      4/2001
WO     WO 01/65995 A2   9/2001

* cited by examiner

*Primary Examiner* — Matthew J Kasztejna
(74) *Attorney, Agent, or Firm* — Arnold International; Jon W. Henry; Bruce Y. Arnold

(57) ABSTRACT

An endoscope includes an illuminator that includes a light emitting surface for illuminating the inside of a living body, an objective optical system for forming an image of a specified object on one side of the objective optical system and illuminated by the illuminator, and a transparent cover that encompasses the illuminator and the one side of the objective optical system. The transparent cover includes an outer surface, and light emitted from the light emitting surface that is reflected by the outer surface satisfies a certain condition that helps prevent rearward dispersed light caused by scratches on, or substances adhering to, the external surface of the transparent cover from entering the entrance pupil of the objective optical system. The endoscope may also include a member for partially shielding the light emitted from the light emitting surface so as to limit the direction in which light is directed from said light emitting surface to the transparent cover.

5 Claims, 7 Drawing Sheets

ENDOSCOPE WITH DECREASED STRAY LIGHT EFFECT THAT INCLUDES A LIGHT SHIELDING MEMBER THAT DOES NOT PASS ANY LIGHT RAYS EMITTED FROM AN ILLUMINATOR

This application claims benefit under 35 U.S.C. §119 of JP 2005-189,346, filed Jun. 29, 2005, the contents of which are hereby incorporated by reference.

TECHNICAL FIELD OF THE INVENTION

The present invention relates to an endoscope for viewing the inside of a body.

BACKGROUND OF THE INVENTION

In recent years, in areas of medical treatment and in industrial applications, the use of endoscopes has been broadly adopted. In particular, broad use has been made of endoscopes with improved insertability to positions where observations of objects are made, and because the distance from the observed object to the observation unit is set at a fixed distance for ease of observation, the tip of the insertion part of the endoscope is fitted with an illuminator and an imaging device, as well as with a transparent cover that encompasses the illuminator and the imaging device.

Conventionally, as an endoscope provided with a transparent cover that encompasses an illuminator and an imaging device provided at the tip of the insertion part of the endoscope, arrangements have been proposed as set forth, for example, in Japanese Laid-Open Patent Application 2001-91860 and WIPO Patent Publication WO 01/65995.

Japanese Laid-Open Patent Application 2001-91860 discloses a capsule endoscope, and WIPO Patent Publication WO 01/65995 discloses an imaging device for a capsule endoscope. A cross-sectional view of the capsule endoscope of Japanese Laid-Open Patent Application 2001-91860 is shown in FIG. 12, and a cross-sectional view of the imaging device for a capsule endoscope of Patent Publication WO 01/65995 is shown in FIG. 13.

As shown in FIG. 12, using the notations of Japanese Laid-Open Patent Application 2001-91860, the capsule endoscope thereof includes an objective lens 22 within a hemispheric transparent cover 17 and an image sensor 111 that continuously receives an updated image formed by the objective lens 22 using light provided by light emitting diodes (LEDs) 30, 30 that surround the objective lens 22.

In addition, using the notations of WIPO Patent Publication WO 01/65995, FIG. 13 shows the capsule endoscope thereof that is constructed with an approximately hemispheric transparent cover 21, a CMOS image-forming camera 24 that detects an object image formed by the optical system 22, and illuminators 23, 23 formed of white light LED light sources, or similar light sources, that illuminate the inside of a body cavity that reflects light through the optical system 22 to form the object image on the CMOS image-forming camera 24.

However, with regard to the construction related to the elements noted above of Japanese Laid-Open Patent Application 2001-91860 and WIPO Patent Publication WO 01/65995, with an endoscope in which an illuminator and an objective optical system are provided on the inside of a transparent cover, problems may develop as follows.

When an endoscope constructed as described in Japanese Laid-Open Patent Application 2001-91860 or in WIPO Patent Publication WO 01/65995 is inserted into the body cavity of a subject for the purpose of diagnosis, as the endoscope proceeds within the body cavity, the outer surface (i.e., the surface of the transparent cover against the object part intended to be observed) may become completely covered with various light-dispersing substances, such as digestive fluids, viscous membranes, and so on.

In addition, the transparent cover is made from a relatively soft material in order to prevent breakage of the transparent cover. However, because the cover material is soft, damage of a minute character, such as scratches, may easily occur on the outer surface of the transparent cover.

Because of this, if the illumination light emitted from the endoscope illuminator reaches the outer surface of the transparent cover that has been damaged or covered by light-dispersing substances, the illumination light may be scattered or reflected back to the inside of the transparent cover as what is termed herein as "rearward-dispersed" light. Such rearward-dispersed light, if transmitted through the image-forming optics within the field of view, including through the entrance pupil of the objective optical system, will result in this light interfering with, and distorting, the desired object image. Thus, such rearward-dispersed light is a major obstacle in obtaining the desired observational information.

BRIEF SUMMARY OF THE INVENTION

The present invention relates to an endoscope designed so that, if the outer surface of the transparent cover is damaged or covered by substances that result in the illumination light being reflected or scattered back to the inside of the transparent cover, this light will not be incident onto the objective optical system so as to interfere with or distort the desired object image, and thus the desired observational information can be obtained.

BRIEF DESCRIPTION OF THE DRAWINGS

The present invention will become more fully understood from the detailed description given below and the accompanying drawings, which are given by way of illustration only and thus are not limitative of the present invention, wherein.

DETAILED DESCRIPTION

An explanation is provided concerning the operational effects of the present invention before considering particular embodiments of the invention. First of all, an explanation is provided concerning the angle $\alpha$, which is the angle a light ray reflected at a point on the external surface of a transparent cover after being emitted as a light ray Q perpendicularly from a light emitting surface of an illuminator makes with a line drawn from the same point on the external surface of the transparent cover to the center of the entrance pupil of the objective optical system.

Figure 1:
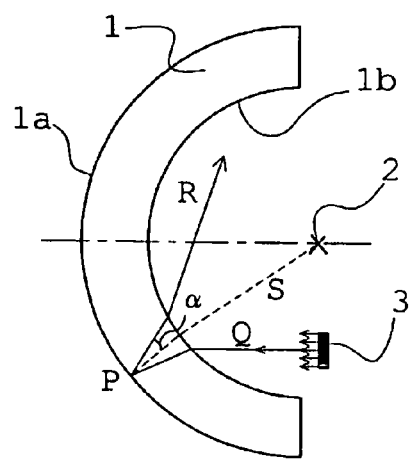
FIG. 1 is a cross-sectional view of the basic construction of the tip of an endoscope of the present invention along the optical axis from the center of the entrance pupil of an objective optical system to the outer surface of a transparent cover.

FIG. 1 is a cross-sectional view of the basic construction of the tip of an endoscope of the present invention along the optical axis from the center of the entrance pupil 2 of an objective optical system to the outer surface of a transparent cover 1. The endoscope of the present invention shown in FIG. 1 includes an illuminator having a light emitting surface 3 for illuminating the inside of a living body, and an objective optical system (shown by the center of its entrance pupil 2 in FIG. 1) for forming an image of a specified object on one side of the objective optical system and illuminated by the illuminator, an imaging device (not shown in FIG. 1) for detecting the image, and the transparent cover 1 which encompasses the illuminator and one side of the objective optical system.

The endoscope of the present invention shown in FIG. 1 is constructed so that the outer surface 1a and the inner surface 1b of the transparent cover 1 are each hemispherical surfaces that are rotationally symmetric about the optical axis that passes through the center of the entrance pupil 2 of the objective optical system, and is also constructed so that the spherical center of the external surface 1a of the transparent cover 1 is coincident with the center of the entrance pupil 2. The light emitting surface 3 is arranged at the periphery of the objective optical system.

Also, the endoscope of the present invention satisfies the following Condition (1):

$$10° \leq \alpha \qquad \text{Condition (1)}$$

where $\alpha$ is the angle formed by a light ray R having a wavelength 546.07 nm that has been specularly reflected at a point P on the outer surface 1a of the transparent cover 1 after being emitted perpendicularly as light ray Q from the light emitting surface 3 of the illuminator with a line drawn from said point on the external surface of the transparent cover to the center of the entrance pupil of the objective optical system.

By the angle $\alpha$ being calculated for light rays of the light beam emitted from all of the points of the light emitting surface 3 and satisfying Condition (1) by adjusting the positional relationship between the center of the entrance pupil 2 of the objective optical system and the light emitting surface 3 of the illuminator, even in cases where there is damage to, or light dispersing substances on, the external surface 1a of the transparent cover 1, light that is dispersed rearward into the objective optical system from the damaged surfaces or from the light-dispersing substances on the external surface 1a of the transparent cover 1 can be prevented, enabling appropriate observation of an imaged object.

In addition, although the explanation above related to FIG. 1 concerns a two-dimensional model related to an endoscope having a single illuminator, the explanation is easily expanded to calculations with three dimensions being considered.

Furthermore, in the structure shown in FIG. 1, even in the case where the endoscope has multiple illuminating sources in the illuminator, if the light emitting surfaces 3 of the illuminator are arranged so as to be rotationally symmetric about the optical axis of the objective optical system, in determining the positional relationship between the center of the entrance pupil 2 of the objective optical system and the light emitting surfaces 3 of the illuminator, and considering first one of the illuminators, the objective can be achieved by calculating only a single angle $\alpha$, and a brighter endoscope can be realized.

In addition, in the case where the transparent cover 1 is not rotationally symmetric about the optical axis of the objective optical system, or in the case where the position of multiple illuminators are not rotationally symmetric about the optical axis of the objective optical system, concerning all of the illuminators, there is a need to individually obtain the angle $\alpha$ relative to the light ray Q emitted from the light emitting surface 3. In this case as well, because in terms of the applicable principle, the angle $\alpha$ is calculated relative to the light ray Q, then concerning the respective illuminators, if adjustment is made of the positional relationship between light emitting surface 3 of the illuminator and the center of the entrance pupil 2 of the objective optical system, the objective can be achieved.

The explanation above relates to FIG. 1 considering that there is no damage to, or light-dispersing substances on, the external surface of the transparent cover of the endoscope. However, in considering a case in which there is damage to or dispersed substances on the external surface of the transparent cover of the endoscope, consideration is given to conditions that sufficiently minimize the amount of rearward-dispersed light, such as caused by damage to the external surface of the transparent cover or by light-dispersing substances on the external surface of the transparent cover of the endoscope and that may enter the entrance pupil of the objective optical system.

Figure 2:
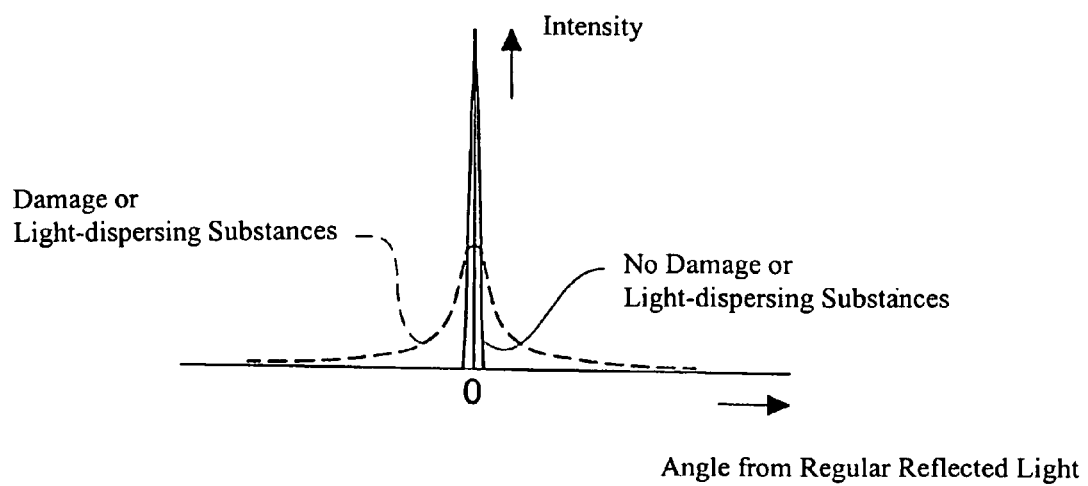
FIG. 2 shows the light intensity distribution of reflected light on the outer surface of a transparent cover of an endoscope.

FIG. 2 shows the light intensity distribution of regularly reflected light on the outer surface of a transparent cover of an endoscope. In FIG. 2, the horizontal axis represents the angle in degrees of the reflected light ray R of FIG. 1 from a center "0" angle defined by regular reflection from the outer surface 1a of the transparent cover 1, and the vertical axis represents the intensity of the light reflected. In FIG. 2, the solid line shows the light intensity distribution of light reflected by the external surface of the transparent cover in the case where there is no damage to, or light-dispersing substances on, the outer surface 1a of the transparent cover 1, and the broken line shows the light intensity distribution of the rearward-dispersed light in the case where there is damage to the outer surface 1a of the transparent cover 1 or where there are light-dispersing substances on the outer surface 1a of the transparent cover 1.

In the case where there is no damage to, or light-dispersing substances on, the outer surface 1a of the transparent cover 1, then, as shown by the solid line of FIG. 2, the fact that the light reflected from the outer surface 1a of the transparent cover 1 has a steep light intensity distribution without, for the most part, becoming broader is already known.

Figure 3A:
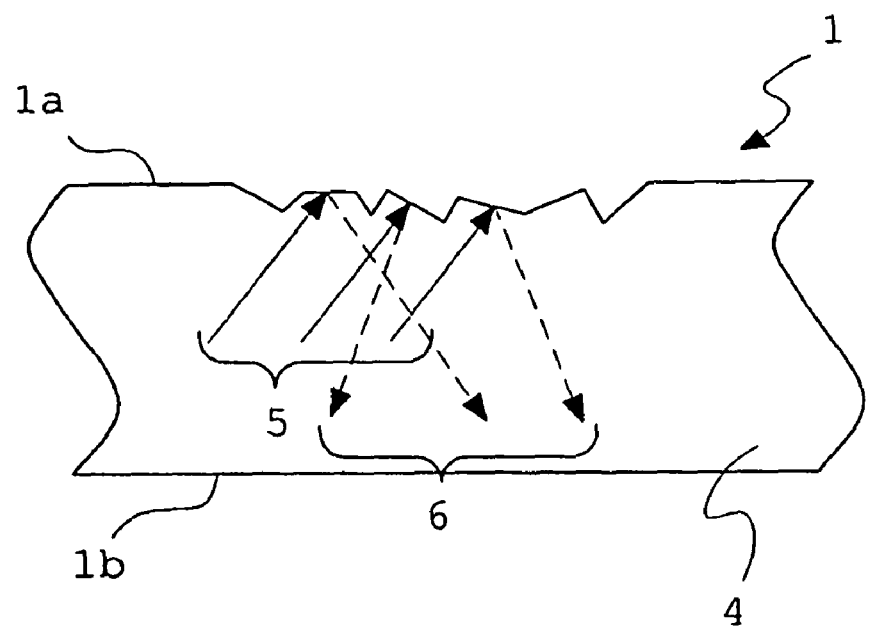
FIG. 3(*a*) is a cross-sectional view of a transparent cover in which damage to the outer surface of the transparent cover affects light reflected on the outer surface, and FIG. 3(*b*) is a cross-sectional view of a transparent cover in which light dispersing matter adhering to the outer surface of the transparent cover affects illumination light that otherwise transmits through the outer surface.

Consideration will now be given to the case in which there is damage to, or substances on, the outer surface 1a of the transparent cover 1. FIG. 3(a) is a cross-sectional view of a transparent cover in which damage to the outer surface of the transparent cover causes light to be reflected at various angles by the outer surface, and FIG. 3(b) is a cross-sectional view of a transparent cover in which matter adhering to the outer surface of the transparent cover affects light that otherwise would transmit through the outer surface, so that some of the light is directed rearward at various angles.

As shown in FIG. 3(a), where there is damage to the outer surface 1a of the transparent cover 1, illumination light rays 5 emitted from the illuminator are dispersed at various angles rearward as light rays 6. The light rays 6 are reflected at the interface of the outer surface 1a of the transparent cover 1 with air, due to the large difference in refractive index between the transparent cover and air.

Figure 3B:
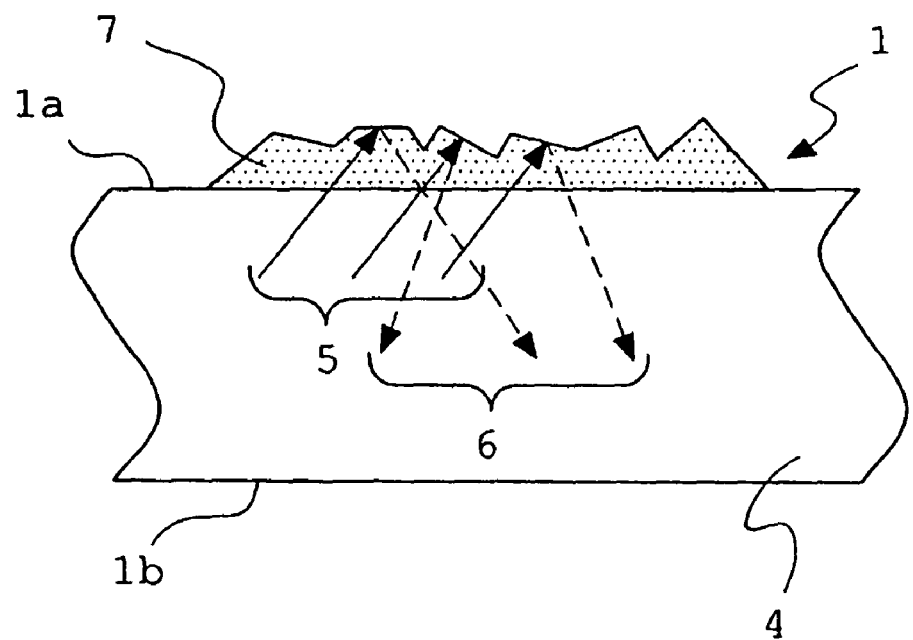

As shown in FIG. 3(b), when light-dispersing substances 7 adhere to the outer surface 1a of the transparent cover 1, some of the illumination light rays 5 emitted from the illuminator are directed rearward as light rays 6 due to light-dispersing substances adhering to the outer surface 1a of the transparent cover 1. These light rays 6 are reflected at the interface of the outer surfaces of the adhering substances with air, due to the large difference in the refractive index of the adhering substances versus that of air. Little reflection occurs at the interface of the transparent cover with the adhering substances, due to there being only small differences in the refractive index of the cover versus that of the adhering substances.

In this manner, in the case where there is damage to, or light-dispersing substances 7 on, the outer surface 1a of the transparent cover 1, the effective outer reflecting surface of a conventional transparent cover is similar to a rough surface that causes some of the illumination light that otherwise would transmit through the outer surface to be directed rearward at various angles over a broad range (hence the term 'rearward-dispersed' light is used herein). As a result, the rearward-dispersed light spreads out as shown by the broken line of FIG. 2 as a broad-based light intensity distribution in comparison to the solid line intensity distribution for the case where there is no damage to, or light-dispersing substances on, the outer surface 1a of the transparent cover 1.

Moreover, in FIG. 2, for the purpose of comparing the broadening of the light distribution, the light intensity distributions for regularly reflected light and rearward-dispersed light are shown as overlapping curves near the center "0" angle position, but the particular relative amplitudes shown are merely exemplary and are subject to variation based on the particulars of the damage to, or the light-dispersing substances on, the outer surface 1a of the transparent cover 1.

Next, in considering the broadening of the distribution of the rearward-dispersed light, consideration is given to the conditions in which the amount of rearward-dispersed light that is then incident on the center of the entrance pupil of the objective optical system is reduced. This will be considered with reference to FIG. 4 that is a cross-sectional view of the basic construction of the tip of an endoscope of the present invention along the optical axis from the center of the entrance pupil of an objective optical system to the outer surface of a transparent cover that has the same construction as that of FIG. 1.

Figure 4:
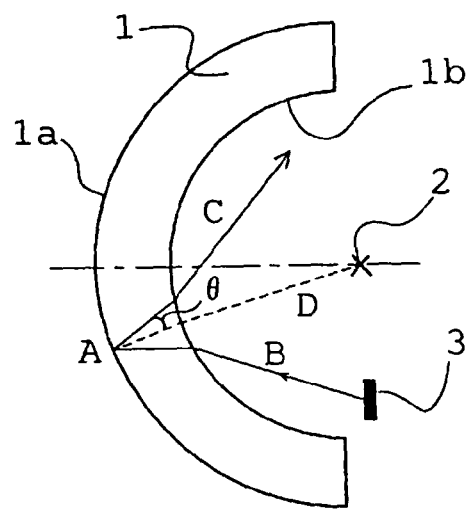
FIG. 4 is a cross-sectional view of the basic construction of the tip of an endoscope of the present invention along the optical axis from the center of the entrance pupil of an objective optical system to the outer surface of a transparent cover that has the same construction as that of FIG. 1.

As shown in FIG. 4, a light ray B emitted at a selected angle from a point on the light emitting surface 3 of the illuminator is incident on the outer surface 1a of the transparent cover 1 at a point A where it is reflected as a light ray C, and the angle formed at point A by the reflected light ray C and a line drawn from said point A to the center of the entrance pupil 2 of the objective optical system is θ. If the angle θ is greater than the maximum distribution angle of the rearward-dispersed light, then the amount of rearward-dispersed light reflected from the outer surface 1a of the transparent cover 1 into the objective optical system will be small.

Figure 5:
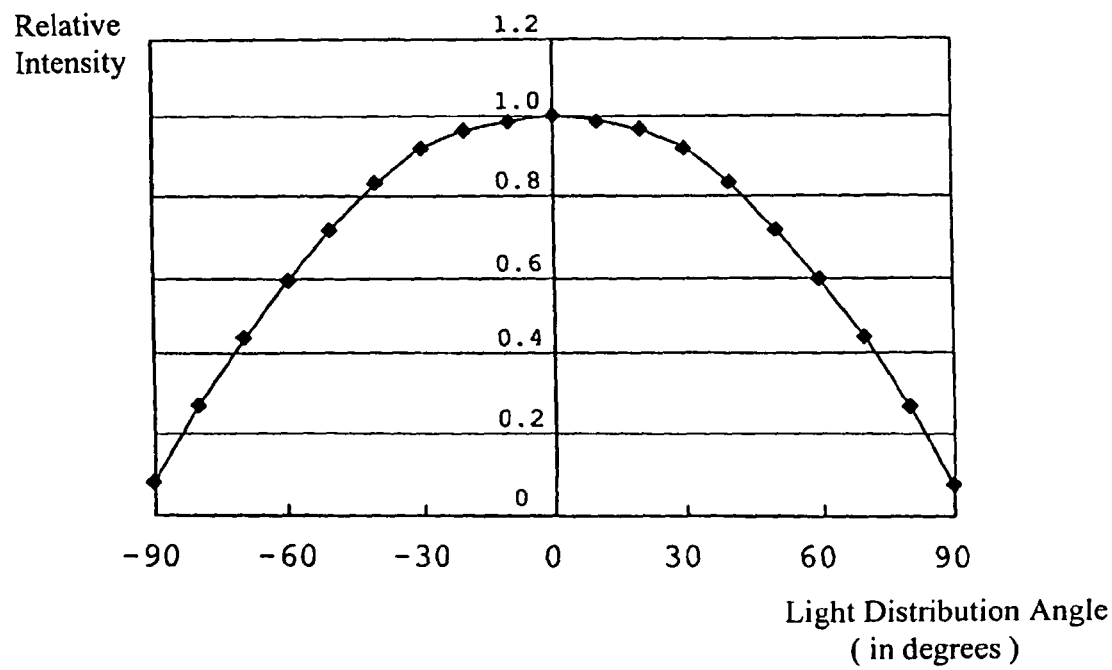
FIG. 5 is a graph of the angular distribution of light intensity emitted by a white light LED.

The light intensity distribution of the illuminator used in the endoscope is a Gaussian distribution with the peak intensity being at a zero degree angle (0°) as measured from the surface normal, which corresponds to the peak intensity being in a direction that is perpendicular to the light emitting surface. FIG. 5 is a graph of the angular distribution of light intensity of a white light LED. The white light LED has fluorescent light-dispersing particles positioned forward of a light emitting diode in order to provide white light illumination. In FIG. 5, the horizontal axis is the light distribution angle (in degrees) as measured from the surface normal, and the vertical axis shows the relative intensity of illumination (i.e., normalized to 1.0 at the peak intensity) at the various distribution angles. If the illuminator is formed of a light-dispersing element in front of a light emitting, terminal surface of a light guide, the light intensity distribution is also that shown in FIG. 5.

If the intensity of light incident normal (i.e., perpendicular) to the outer surface of the transparent cover is normalized to be one, then the intensity of the light dispersed rearward is 0.05, and, to the extent that the angles of light rays incident on the outer surface of the transparent cover depart from this perpendicular incidence (i.e., "0" on the horizontal axis of FIG. 5), the intensity will be reduced. Therefore, it is sufficient to consider only light rays with the distribution angle of "0", since the intensity of illumination light is a maximum at this distribution angle.

Furthermore, satisfying Condition (1) above controls rearward-dispersed light even though the angle θ in FIG. 4 is different from the angle α explained above with reference to FIG. 1. In other words, if the angle α is greater than the maximum angle of the rearward-dispersed light beam (as measured at the 10% intensity profile points of the light beam), then the intensity of the rearward-dispersed light ray B of FIG. 4 that is incident on the entrance pupil of the objective optical system will be reduced to the point that it is not a problem (as contrasted with the intensity of rearward-dispersed light that would be incident on the entrance pupil of the objective optical system if Condition (1) is not satisfied). These considerations apply generally where the outer surface 1a of the transparent cover 1 is effectively a rough surface (as occurs with either scratches on, or light-dispersing matter adhering to, the outer surface 1a).

Figure 6:
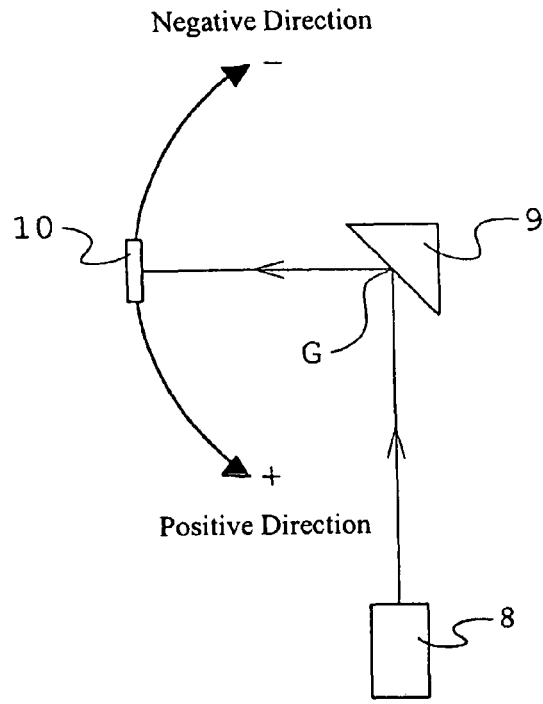
FIG. 6 is a diagram used to explain the construction of a measuring device for measuring the angular distribution of rearward-dispersed light.

FIG. 6 is used to explain the construction of a measuring device for measuring the angular distribution of rearward-dispersed light. In FIG. 6, the He—Ne laser oscillator 8 is arranged so that the emitted light beam is incident at an angle of forty-five degrees to the reflecting surface of a prism 9. The distance to the incident point G of the prism 9 from the laser light emission aperture is 600 mm. A detector 10 for measuring the rearward-dispersed light is arranged so as to rotate around the center point G. The distance from the point G to the light-receiving surface of the detector 10 is 200 mm. Making the rotational angle of the detector 10 at the time that the laser light reflected at G is incident on the light-receiving surface of the detector 10 to be 0°, and considering the counterclockwise direction to be the positive direction, then measurement is made of the illumination at the light-receiving surface from respective angles while rotating the detector 10.

First, measurements are made in a state in which there are no light-dispersing substances on the prism surface. Subsequently, new measurements are made with light-dispersing substances distributed on the prism surface. The light-receiving surface of the detector is formed in a circular shape having a diameter of 15 mm, and because the area of the light-receiving surface is sufficiently great, the influence of the laser light speckle is averaged, and can largely be ignored.

In the subject measurement conditions, with laser light being emitted from the He—Ne laser oscillator 8, rearward-dispersed light that is reflected from the interfaces of the matter that is distributed on the surface of the prism 9 and air is led to the detector 10. On the other hand, in the present invention, because the illumination light emitted from the illuminator is reflected rearward by interfaces of substances adhering to the surface of the transparent cover with air, although the subject measurement conditions are different from those of the present invention, because the refractive indexes of the light-dispersing substances are nearly the same as that of the transparent cover, there is little rearward-dispersion of light at interfaces of the transparent cover with substances on the cover.

Figure 7:
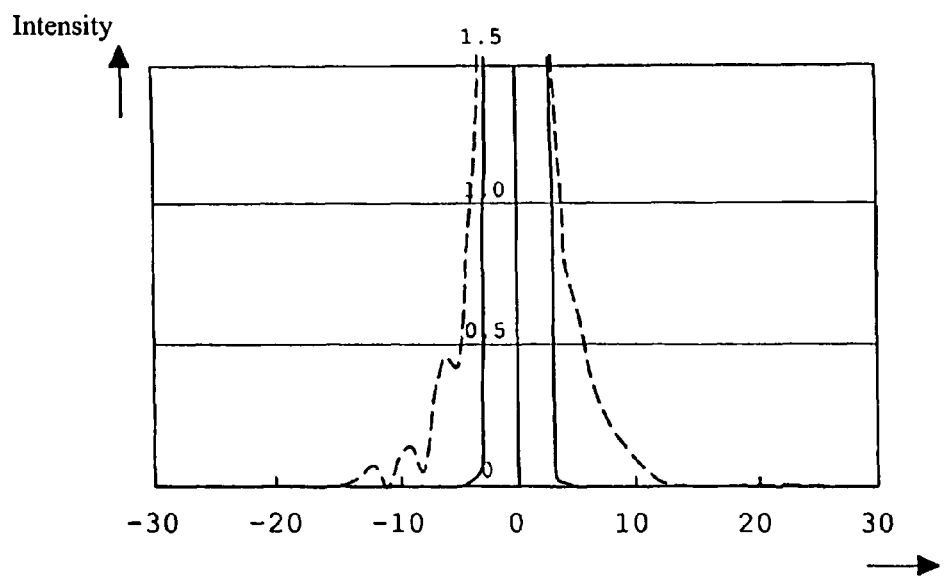
FIG. 7 is a graph of the angular distribution of measured rearward-dispersed light.

FIG. 7 is a graph of the angular distribution of the light at the surface of the prism 9. In FIG. 7, the horizontal axis shows the angle (as measured from the surface normal) of regular reflected light, and the vertical axis shows the light intensity (in arbitrary units). The solid line shows the angular distribution of light in the case when there is no adherence of light-dispersing substances on the surface of the prism 9, and the broken line shows the angular distribution of light when there is adhesion of light-dispersing substances on the surface of the prism 9.

According to FIG. 7, when light-dispersing substances are adhering to the surface of the prism 9, there is a broadening of the intensity profile (as compared to the intensity profile of regularly reflected light with no light-dispersing substances on the surface of the prism 9) by about plus and minus ten degrees in the case of the beam width being measured at 10% of the peak intensity. Thus, if the angle α of FIG. 1 is greater than ten degrees, the light from the illuminator that will be incident on the entrance pupil of the objective optical system after being dispersed rearward by substances adhering to the surface of the prism 9 will usually be sufficiently small to not cause a problem.

The maximum angle of the rearward-dispersed light is not ordinarily fixed, and instead changes somewhat depending upon the type of adhering substance, the state of adhesion, the state of damage, and other factors. Due to this variability in the maximum angle of rearward-dispersed light, it is preferred that the angle α be fifteen degrees or greater.

Four embodiments will now be discussed in detail with further reference to the drawings and with reference to various tables.

Embodiment 1

Figure 8:
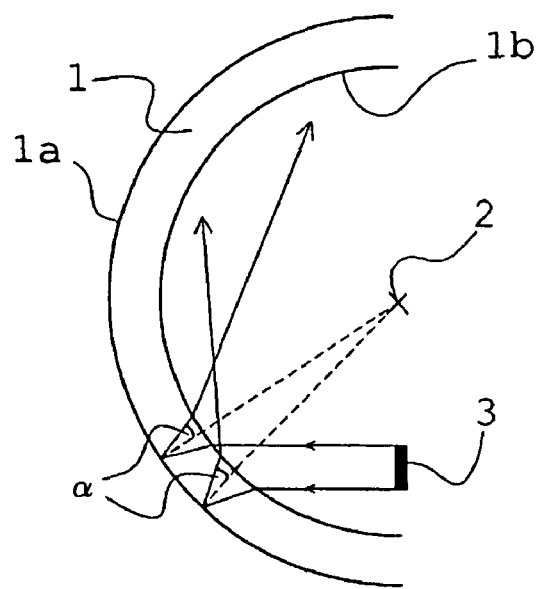
FIG. 8 is a cross-sectional view of the tip of the endoscope of Embodiment 1 of the present invention.

FIG. 8 is a cross-sectional view of the tip of the endoscope of Embodiment 1 of the present invention. In order to simplify the following explanation, reference is made to a two-dimensional model.

The endoscope of Embodiment 1 includes a light emitting surface 3 of an illuminator that illuminates the inside of a living body and an objective optical system (not shown in FIG. 8) that forms an image of a specified endoscope object position illuminated by the illuminator, an imaging device (not shown in FIG. 8) that acquires an image of the specified endoscope object position, and a transparent cover 1 that encompasses the illuminator and the object position side of the objective optical system.

With the endoscope of Embodiment 1, the endoscope transparent cover 1 has a hemispheric shape with the outer surface of the transparent cover 1a and the inner surface 1b both being formed as rotationally symmetric spherical surfaces about an optical axis that passes through the center of the entrance pupil 2 of the objective optical system. Additionally, the endoscope is constructed so that the spherical center of the outer surface 1a of the transparent cover 1 is coincidental with the center of the entrance pupil 2 of the objective optical system. The radius of curvature of the outer surface of the transparent cover 1 is 5.5 mm, the radius of curvature of the inner surface 1b is 4.5 mm, and the thickness is 1 mm. In addition, the refractive index of the material of the transparent cover 1 relative to the e-line (546.07 nm) is 1.527.

In addition, the light emitting surface 3 of the illuminator is arranged at the periphery of the objective optical system in a plane perpendicular to the central axis of the endoscope and passing through the center of the entrance pupil 2. The shortest distance from the central axis of the endoscope to the light emitting surface is 2.8 mm, and the longest distance from the central axis of the endoscope to the light emitting surface is 3.6 mm.

Table 1 below shows the values of the angle α, as described previously, calculated for light rays emitted from the light emitting surface at various distances from the central axis of the endoscope of Embodiment 1 for light of wavelengths at the e-line.

TABLE 1

| Distance (mm) From Central Axis to the Light Emitting Diode Surface | Angle α (°) For Light Rays at the e-line |
|---|---|
| 2.8 | 19.5 |
| 2.9 | 20.2 |
| 3.0 | 20.9 |
| 3.1 | 21.7 |
| 3.2 | 22.4 |
| 3.3 | 23.1 |
| 3.4 | 23.9 |
| 3.5 | 24.6 |
| 3.6 | 25.4 |

From Table 1, it is clear that the value of the angle α becomes larger as the distance from the central axis increases. In the endoscope of Embodiment 1, because the angle α is much greater than the lower limit of ten degrees of Condition (1) above, the amount of rearward dispersed light that passes to the entrance pupil due to dispersed substances or scratches on the outer surface of the transparent cover can be made smaller.

Embodiment 2

Figure 9:
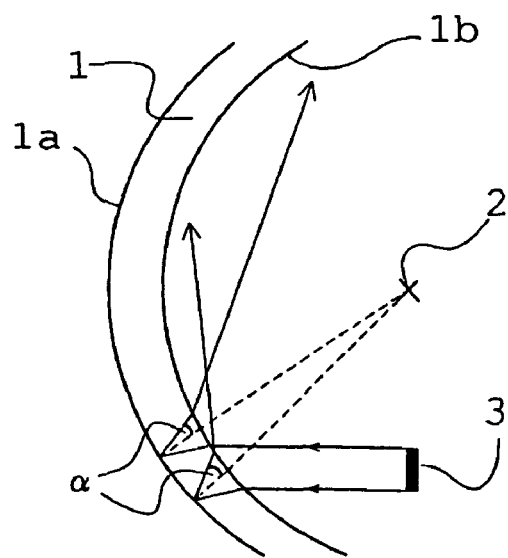
FIG. 9 is a cross-sectional view of the tip of the endoscope of Embodiment 2 of the present invention.

FIG. 9 is a cross-sectional view of the tip of the endoscope of Embodiment 2 of the present invention. In order to simplify the following explanation, reference is made to a two-dimensional model. The construction of Embodiment 2 is very similar to that of Embodiment 1 described above.

In the endoscope of Embodiment 2, the transparent cover 1 of the endoscope is formed so that both the inner surface 1b and the outer surface 1a of the transparent cover 1 are rotationally symmetric about the central axis of the endoscope and are elliptical surfaces in cross-section. A central axis z is coincident with the optical axis of the endoscope and denoting the axes perpendicular to the optical axis as the x and y axes, the shape of the rotationally symmetric aspheric outer surface 1a is given by Equation (1) below:

$$Z=(Y^2/r)/[1+\{1-(K+1)(Y/r)^2\}^{1/2}] \qquad \text{Equation (1)}$$

where
- Z is the length (in mm) of a line drawn from a point on the aspheric surface at distance y from the optical axis to the tangential plane of the aspheric surface vertex,
- r is the radius of curvature of the aspheric surface on the optical axis,
- Y is the distance (in mm) from the optical axis, and
- K is the eccentricity.

The radius of curvature r of the outer surface 1a of the transparent cover 1 is 6.2443 mm, and the eccentricity K is 0.1.

In addition, the thickness of the transparent cover on the center axis is 1 mm, and the refractive index of the material of the transparent cover at the e-line is 1.527.

The center of the entrance pupil 2 of the objective optical system is positioned 4.7 mm from the inner surface 1b of the transparent cover 1 on the central axis of the endoscope. In addition, the light emitting surface 3 of the illuminator is in a plane that is perpendicular to the central axis of the endoscope and that passes through the center of the entrance pupil 2. The distance to the closest part of the light emitting surface 3 from the central axis of the endoscope is 3.1 mm, and the distance to the farthest part of the light emitting surface 3 from the central axis of the endoscope is 3.9 mm.

Table 2 below shows the values of the angle α, as described previously, calculated for light rays emitted from the light emitting surface at various distances from the central axis of the endoscope of Embodiment 2 for light of wavelengths at the e-line.

TABLE 2

| Distance (mm) From Central Axis to the Light Emitting Diode Surface | Angle α (°) For Light Rays at the e-line |
|---|---|
| 3.1 | 20.0 |
| 3.2 | 20.7 |
| 3.3 | 21.4 |
| 3.4 | 22.1 |
| 3.5 | 22.8 |
| 3.6 | 23.6 |
| 3.7 | 24.3 |
| 3.8 | 25.0 |
| 3.9 | 25.8 |

From Table 2 it is clear that as the distance from the central axis of the endoscope increases, the value of the angle α also increases.

Here, consideration is given to the fact that the entrance pupil of the objective optical system is positioned on a surface perpendicular to the optical axis and so that the amount of rearward dispersed light incident on the objective optical system is sufficiently small. In order to keep the outer diameter of the endoscope small, it is preferable that the following Condition (2) be satisfied:

$$15° \leq \alpha \leq 30° \qquad \text{Condition (2)}$$

where
α is the angle as defined above.

If the lower limit of Condition (2) above is not satisfied, sometimes the amount of rearward dispersed light incident on the objective optical system may not be sufficiently small. On the other hand, if the upper limit of Condition (2) above is not satisfied, the distance between the center of the entrance pupil 2 of the objective optical system and the light emitting surface of the illuminator will become too great, so that the outer diameter of the endoscope cannot be made small.

According to the endoscope of Embodiment 2, the positional relationship between the center of the entrance pupil 2 of the objective optical system and the light emitting surface 3 of the illuminator is constructed so as to satisfy Condition (2), and in addition to enabling the minimization of the amount of rearward dispersed light incident on the objective optical system that is caused by dispersed substances adhering to or scratches on the outer surface 1a of the transparent cover 1, an endoscope with a small outer diameter can also be realized.

Embodiment 3

Figure 10:
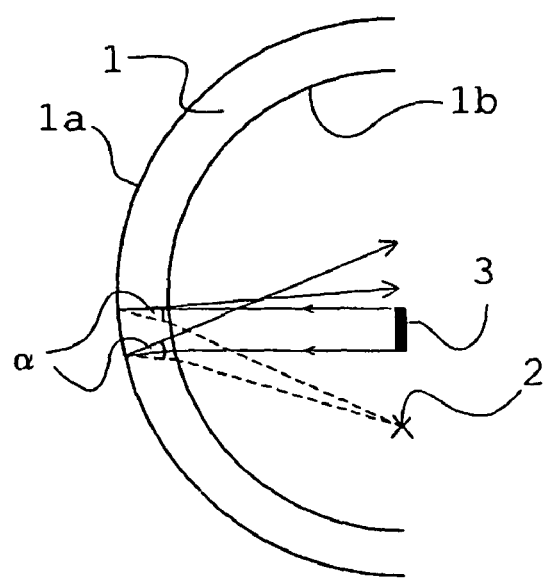
FIG. 10 is a cross-sectional view of the tip of the endoscope of Embodiment 3 of the present invention.

FIG. 10 is a cross-sectional view of the tip of the endoscope of Embodiment 3 of the present invention. In order to simplify the following explanation, reference is made to a two-dimensional model.

In the endoscope of Embodiment 3, the transparent cover 1 of the endoscope is formed as a hemisphere, with the radius of curvature of the outer surface 1a being 5.5 mm, the radius of curvature of the inner surface 1b being 4.5 mm, and the thickness of the transparent cover 1 being 1 mm.

In addition, the refractive index at the e-line of the material of the transparent cover 1 is 1.527. The center of the entrance pupil 2 of the objective optical system lies on a straight line that is perpendicular to the central axis of the endoscope that passes through the spherical center of the outer surface 1a of the transparent cover 1 and is at a distance of 2.5 mm from the central axis along the straight line.

The light emitting surface 3 of the illuminator is in a plane that is perpendicular to the central axis of the endoscope and that passes through the spherical center of the outer surface 1a of the transparent cover 1, and is arranged on the periphery of the objective optical system. The distance to the light emitting surface 3 from the central axis of the endoscope is measured as positive in the direction facing the center of the entrance pupil 2, with the closest part being at 0.2 mm and the farthest part being at 1.0 mm.

Table 3 below shows the values of the angle α, as described previously, calculated for light rays emitted from the light emitting surface at various distances from the central axis of the endoscope of Embodiment 3 for light of wavelengths at the e-line.

TABLE 3

| Distance (mm) From Central Axis to the Light Emitting Diode Surface | Angle α (°) For Light Rays at the e-line |
|---|---|
| 0.2 | 17.1 |
| 0.3 | 17.9 |
| 0.4 | 18.7 |
| 0.5 | 19.5 |
| 0.6 | 20.2 |
| 0.7 | 21.0 |
| 0.8 | 21.8 |
| 0.9 | 22.6 |
| 1.0 | 23.4 |

From Table 3 it is clear that as the distance from the central axis to the light emitting diode surface of the endoscope increases, the value of the angle α also increases.

In Embodiment 3, because the angle α is sufficiently greater than the minimum ten degree angle for rearward dispersed light, the amount of light incident on the objective optical system of the rearward dispersed light caused by dispersed substances adhering to or scratches on the outer surface of the transparent cover can be made smaller.

Embodiment 4

Figure 11:
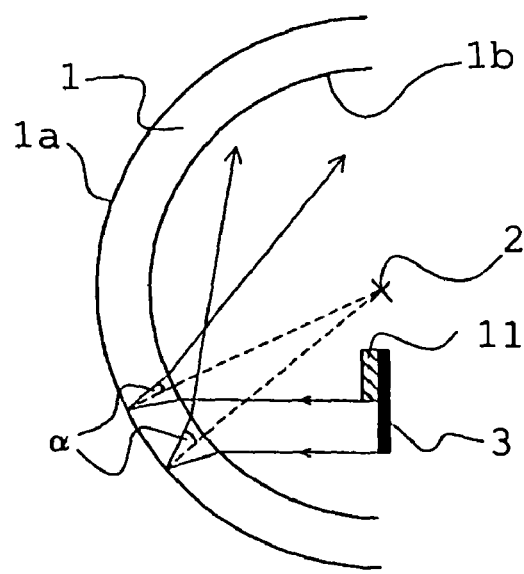
FIG. 11 is a cross-sectional view of the tip of the endoscope of Embodiment 4 of the present invention.
Figure 12:
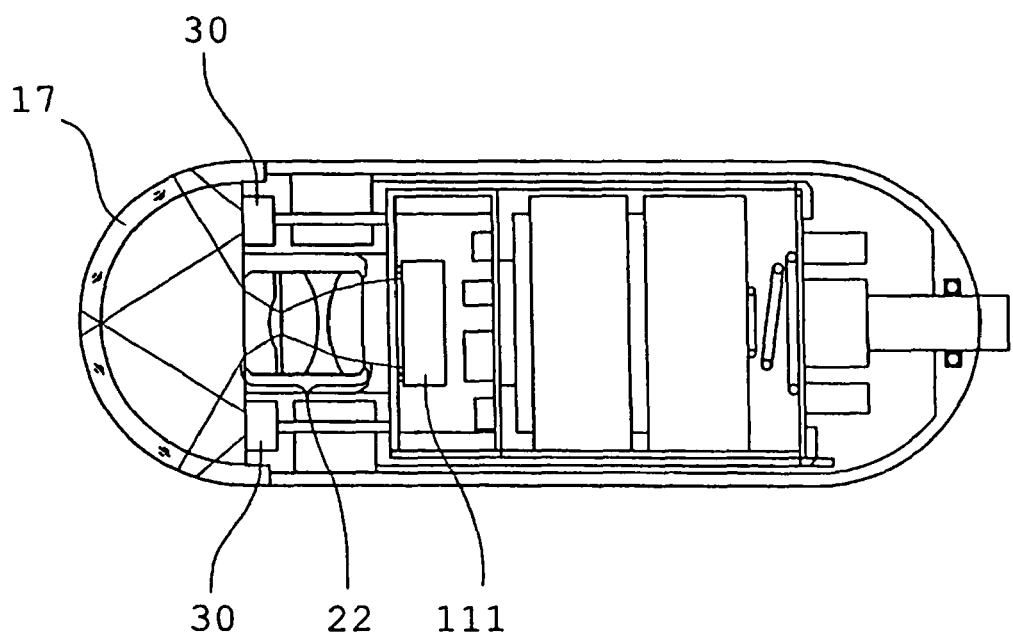
FIG. 12 is a cross-sectional view of a conventional capsule endoscope.
Figure 13:
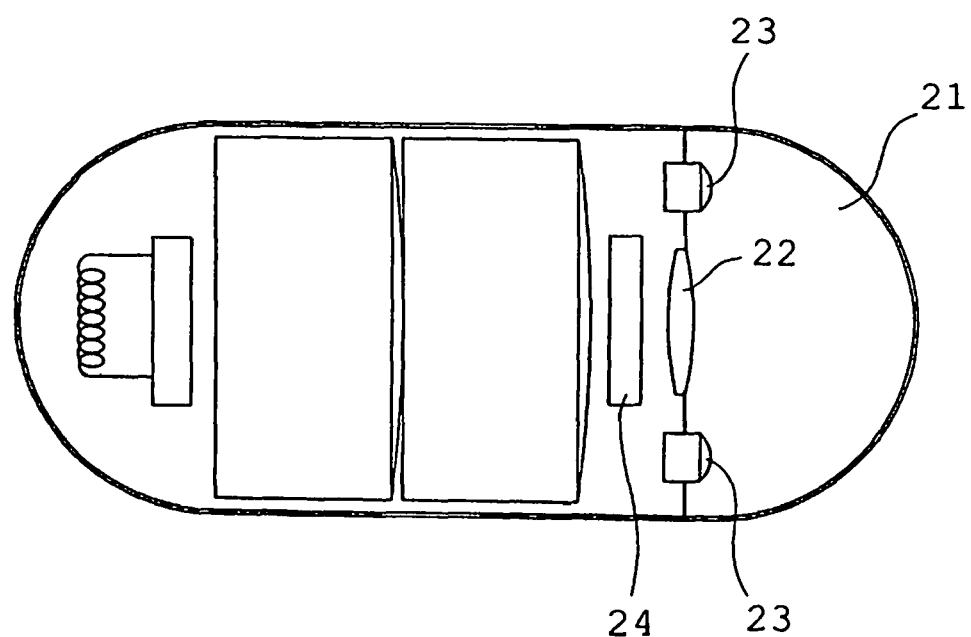
FIG. 13 is a cross-sectional view of the imaging device for another conventional capsule endoscope.

FIG. 11 is a cross-sectional view of the tip of the endoscope of Embodiment 4 of the present invention. In order to simplify the following explanation, reference is made to a two-dimensional model.

The construction of Embodiment 4 is very similar to that of Embodiment 1 described above. However, in Embodiment 4, a light shielding member 11 that shields a portion of the light emitting surface 3 is provided. As seen in FIG. 11, the light shielding member does not pass any light rays that are incident on the light shielding member from the light emitting surface of the illuminator. In addition, the light emitting surface of the illuminator of Embodiment 4 uses measurements which are large in comparison with those of the other embodiments.

In Embodiment 4, the transparent cover 1 of the endoscope is hemispherical, and the outer surface 1a and inner surface 1b of the transparent cover 1 are each formed as surfaces that are rotationally symmetric about the optical axis that passes through the center of the entrance pupil of the objective optical system, with the structure being such that the spherical center of the outer surface 1a of the transparent cover 1 coincides with the center of the entrance pupil 2 of the objective optical system.

The radius of curvature of the outer surface 1a of the transparent cover 1 is 5.5 mm, the radius of curvature of the inner surface 1b is 4.5 mm, and the thickness of the transparent cover 1 is 1 mm, and the refractive index at the e-line of the material of the transparent cover is 1.527.

In addition, the light emitting surface 3 of the illuminator is in a plane that is perpendicular to the central axis of the endoscope and that passes through the center of the entrance pupil 2 and is arranged on the periphery of the objective optical system. The distance to the closest part of the light emitting surface 3 from the central axis of the endoscope is 1.2 mm, and the distance to the farthest part of the light emitting surface 3 from the central axis of the endoscope is 3.2 mm.

In addition, light shielding member 11 shields a part of the light emitted from the light emitting surface 3. The distance to the closest part of the light shielding member 11 from the central axis of the endoscope is 1.2 mm, and the distance to the farthest part of the light shielding member 11 from the central axis of the endoscope is 2.2 mm.

Table 4 below shows the values of the angle α, as described previously, calculated for light rays emitted from the light emitting surface at various distances from the central axis of the endoscope of Embodiment 4 for light of wavelengths at the e-line.

TABLE 4

| Distance (mm) From Central Axis to the Light Emitting Diode Surface | Angle α (°) For Light Rays at the e-line |
| --- | --- |
| 1.2 | 8.2 |
| 1.3 | 8.9 |
| 1.4 | 9.6 |
| 1.5 | 10.3 |
| 1.6 | 11.0 |
| 1.7 | 11.7 |

TABLE 4-continued

| Distance (mm) From Central Axis to the Light Emitting Diode Surface | Angle α (°) For Light Rays at the e-line |
| --- | --- |
| 1.8 | 12.4 |
| 1.9 | 13.1 |
| 2.0 | 13.8 |
| 2.1 | 14.5 |
| 2.2 | 15.2 |
| 2.3 | 15.9 |
| 2.4 | 16.6 |
| 2.5 | 17.3 |
| 2.6 | 18.0 |
| 2.7 | 18.7 |
| 2.8 | 19.5 |
| 2.9 | 20.2 |
| 3.0 | 20.9 |
| 3.1 | 21.7 |
| 3.2 | 22.4 |

From Table 4 above, it is clear that as the distance from the central axis to the light emitting diode surface of the endoscope increases, the value of the angle α also increases. In addition, within parameters in which the distance to the light emitting surface from the central axis is between 1.2 mm and 1.4 mm, the angle α for light of wavelengths at the e-line is ten degrees or less. And, within parameters in which the distance to the light emitting surface from the central axis of the endoscope is between 1.2 mm and 1.4 mm, a light beam emitted from the light emitting surface 3 of the illuminator does not satisfy Condition (1) above.

In the case where the measurements of the light emitting surface of the illuminator relative to the outer diameter of the endoscope is relatively large, or in the case where, for some reason, the light emitting surface cannot be arranged in an optimal position, the angle α cannot satisfy Conditions (1) and (2) above.

In Embodiment 4, the light shielding member 11 is arranged on the part of the light emitting surface 3 where the value of the angle α for the light emitted from the light emitting surface 3 of the illuminator would be relatively small so that the angle α for the illumination light beam is sufficiently greater than the ten degrees minimum angle of the rearward dispersed light. Therefore, the amount of light incident onto the objective optical system of the rearward dispersed light caused by dispersed substances adhering to or scratches on the outer surface of the transparent cover can be made smaller.

The invention being thus described, it will be obvious that the same may be varied in many ways. Such variations are not to be regarded as a departure from the spirit and scope of the invention. Rather, the scope of the invention shall be defined as set forth in the following claims and their legal equivalents. All such modifications as would be obvious to one skilled in the art are intended to be included within the scope of the following claims.

What is claimed is:

1. An endoscope comprising:
   an illuminator that includes a light emitting surface for illuminating the inside of a living body;
   an objective optical system for forming an image of a specified object on one side of the objective optical system and illuminated by the illuminator, said objective optical system having an optical axis and an entrance pupil having a center on said optical axis;
   a transparent cover that encompasses the illuminator and said one side of the objective optical system and that includes an outer surface; and a light shielding member, that shields a portion of the light emitted from said light emitting surface, is provided on said light emitting surface, said light shielding member does not pass any light rays that are incident on the light shielding member from said illuminator;

wherein the following condition is satisfied:

$$10° \leq \alpha$$

where

α is the angle formed by a light ray having a wavelength of 546.07 nm that has been specularly reflected at a point on the outer surface of the transparent cover after being emitted perpendicularly as a light ray from the light emitting surface of the illuminator with a line drawn from said point on the external surface of the transparent cover to the center of the entrance pupil of the objective optical system.

2. The endoscope of claim 1, wherein the following condition is also satisfied:

$$15° \leq \alpha \leq 30°$$

where

α is defined as set forth previously.

3. An endoscope comprising:

an illuminator that includes a light emitting surface for illuminating the inside of a living body;

an objective optical system for forming an image of a specified object on one side of the objective optical system and illuminated by the illuminator, said objective optical system having an optical axis and an entrance pupil having a center on said optical axis;

a transparent cover that encompasses the illuminator and said one side of the objective optical system and that includes an outer surface, said transparent cover having a center axis; and a light shielding member, that shields a portion of the light emitted from said light emitting surface, is provided on said light emitting surface, said light shielding member does not pass any light rays that are incident on the light shielding member from said illuminator;

wherein the optical axis of the objective optical system is displaced from the center axis of the transparent cover, and the following condition is satisfied:

$$10° \leq \alpha$$

where

α is the angle formed by a light ray having a wavelength of 546.07 nm that has been specularly reflected at a point on the outer surface of the transparent cover after being emitted perpendicularly as a light ray from the light emitting surface of the illuminator with a line drawn from said point on the external surface of the transparent cover to the center of the entrance pupil of the objective optical system.

4. The endoscope of claim 3, wherein the following condition is also satisfied:

$$15° \leq \alpha \leq 30°$$

where

α is defined as set forth previously.

5. An endoscope comprising:

an illuminator that includes a light emitting surface for illuminating the inside of a living body;

an objective optical system for forming an image of a specified object on one side of the objective optical system and illuminated by the illuminator, said objective optical system having an optical axis and an entrance pupil having a center;

a transparent cover that encompasses the illuminator and said one side of the objective optical system and that includes an outer surface; and a light shielding member, that shields a portion of the light emitted from said light emitting surface, is provided on said light emitting surface, said light shielding member does not pass any light rays that are incident on the light shielding member from said illuminator;

wherein the following condition is satisfied:

$$10° \leq \alpha$$

where

α is the angle formed by a light ray having a wavelength of 546.07 nm that has been specularly reflected at a point on the outer surface of the transparent cover after being emitted perpendicularly as a light ray from the light emitting surface of the illuminator with a line drawn from said point on the external surface of the transparent cover to the center of the entrance pupil of the objective optical system.

\* \* \* \* \*